(12) United States Patent
Hartick et al.

(10) Patent No.: US 6,532,276 B1
(45) Date of Patent: Mar. 11, 2003

(54) METHOD AND APPARATUS FOR DETERMINING A MATERIAL OF A DETECTED ITEM

(75) Inventors: Martin Hartick, Bad Nauheim (DE); Frank Cordes, Neustadt (DE)

(73) Assignee: Heimann Systems GmbH, Wiesbaden (DE)

( * ) Notice: Subject to any disclaimer, the term of this patent is extended or adjusted under 35 U.S.C. 154(b) by 0 days.

(21) Appl. No.: 10/046,777

(22) Filed: Jan. 17, 2002

Related U.S. Application Data

(63) Continuation of application No. 09/760,418, filed on Jan. 16, 2001, now abandoned, which is a continuation of application No. 09/645,485, filed on Aug. 25, 2000, now abandoned.

(30) Foreign Application Priority Data

Nov. 13, 1999 (DE) .......................................... 199 54 663

(51) Int. Cl.$^7$ ............................................. G01N 23/207
(52) U.S. Cl. ............................. 378/88; 378/57; 378/90
(58) Field of Search .......................... 378/57, 53, 88, 378/90, 149

(56) References Cited

U.S. PATENT DOCUMENTS

| | | | | |
|---|---|---|---|---|
| 4,956,856 | A | * | 9/1990 | Harding ........................ 378/88 |
| 5,265,144 | A | | 11/1993 | Harding et al. |
| 5,590,169 | A | | 12/1996 | Monteiro |
| 5,917,880 | A | * | 6/1999 | Bjorkholm ................... 378/57 |

FOREIGN PATENT DOCUMENTS

| | | |
|---|---|---|
| DE | 3909147 A1 | 9/1990 |
| DE | 4130039 A1 | 3/1993 |
| DE | 19510168 A1 | 9/1996 |
| EP | 0354045 | 2/1990 |
| WO | 99/66317 | 12/1999 |

OTHER PUBLICATIONS

Bomsdorf, Coherent X–Ray Scatter for Non–Destructive Testing of Works of Art, NDT.net—Dec. 1999, vol. 4, No. 12, pp. 1–10, Proceedings of the 6$^{th}$ Intl. Conf. on "Nondestructive testing and microanalysis for the diagnostics and conservation of the cultural and environmental heritage", Rome, May 17$^{th}$—20$^{th}$, p. 941, 1999 (see p. 4 and figure 1).
Strecker, Automatische Gepackkontrolle mit Rontgenstreustrahlung, Physik in unserer Zeit/Jan. 30, 1999, Nr. 1.
http://www.heimannsystems.com/newsar.htm, accessed Nov. 6, 2001 (see "Worldwide leadership in X–ray diffraction technology confirmed").

* cited by examiner

Primary Examiner—Robert H. Kim
Assistant Examiner—Hoon K. Song
(74) Attorney, Agent, or Firm—Birch, Stewart, Kolasch & Birch, LLP

(57) ABSTRACT

A method for determining the material of a detected item in objects, especially explosives in luggage, using X-ray diffraction. In this method, wherein scatter radiation deflected at the crystal-lattice structure of the material is measured and compared to characteristic energy spectra or diffraction spectra of various explosives, the absorption by the material influences the X-ray diffraction spectrum, so that information is missing, and inaccurate conclusions may be drawn regarding the material. To improve this method, the primary beam of an X-ray source is used for measuring the absorption. The beam passes through the material, and, from the absorption, an average atomic number of the material is determined, and this additional information is used for the identification of material known by comparing the recorded spectra with diffraction spectra. For this purpose, a collimation/detector arrangement preferably has only one collimator (8) and one detector (9), with the collimator (8) having a conically-expanding circular slot (1), which defines a predetermined diffraction angle, and a central blind bore (1) opening toward the x-ray source. First and second detectors (13, 14) are disposed in the bore to detect lower and higher x-ray energy, respectively.

8 Claims, 2 Drawing Sheets

METHOD AND APPARATUS FOR DETERMINING A MATERIAL OF A DETECTED ITEM

CROSS-REFERENCE TO RELATED APPLICATION

This application is a continuation of application Ser. No. 09/760,418 filed Jan. 16, 2001 now abandoned, which is a continuation of application Ser. No. 09/645,485 filed Aug. 25, 2000 now abandoned.

FIELD OF THE INVENTION

The invention relates to a method wherein the material is x-rayed by a primary beam that is diffracted at the material and an apparatus for determining the material of a detected item in an object.

BACKGROUND OF THE INVENTION

To assure safety in situations such as air travel, it is necessary to check luggage (object) with travel items (items), particularly for explosive substances or agents, by employing the most modern technical equipment.

A useful technique for checking for explosives is X-ray diffraction, in which X-rays scattered at the crystal structure of an item are measured and compared to the characteristic energy spectra of different explosives, for example. The spectra can provide an indication of the presence of an explosive, and can thereby provide information about the nature of an explosive material in the object.

Apparatuses and methods that operate according to this principle are known from, for example, DE 195 10 168 A1, EP 0 354 045 A2 and U.S. Pat. No. 4,956,856. A drawback of these methods is that absorption of the X-rays by, for example, the object and item affects the X-ray diffraction spectrum. Consequently, if spectral information is missing due to absorption, inaccurate conclusions may be drawn regarding the type of material and the identification of the substances examined.

BRIEF SUMMARY OF THE INVENTION

It is an object of the invention to provide a method and an apparatus of the type originally mentioned above, with which materials of an item can be identified unambiguously.

The above object generally is achieved according to the first aspect of the invention by a method for determining the material of a detected item in an object that comprises the steps of irradiating the material with a primary X-ray beam; measuring a diffraction spectrum of the material, with the spectrum comprising X-rays of the primary beam diffracted from the material; measuring the X-ray absorption of the material and an average atomic number of the material by measuring X-rays of the primary beam transmitted through the material; and comparing the measured diffraction spectrum and measured average atomic number of the material to known diffraction spectra and known average atomic numbers of known materials to determine the material.

The apparatus for determining the material of a detected item in an object comprises a diffraction apparatus and a computer connected thereto, wherein the diffraction apparatus comprises an x-ray source and a collimator/detector arrangement, including a detector located behind a collimator, with the detector comprising an X-ray sensitive surface oriented toward the collimator. The collimator defines a central, blind-bore opening and at least one conically expanding slot, with the at least one conically expanding slot defining a predetermined angle and being oriented toward the X-ray sensitive surface of the detector. The central opening is closed to the detector and has first and second detection devices mounted therein, with the first and second detection devices being connected to the computer detecting relatively lower and relatively higher energy X-rays, respectively, and being spaced in the central opening with the second detection device located behind the first detection device.

The concept underlying the invention is to obtain additional information about the absorption behavior of the materials from the central X-ray beam during a diffraction measurement, and to make this information available along with the diffraction spectrum for evaluation and identification of the material.

The diffraction apparatus which as indicated above, generally comprises a collimator/detector arrangement and an X-ray source for generating a central beam or primary beam that is aimed at the arrangement. According to the invention, the collimator of the collimator/detector arrangement has a central, blind-bore open to and facing the X-ray source, in which first and second detector devices are arranged, with the first and second detector devices being spatially separate from each other and disposed one behind the other. The detector device that is impacted first by the primary beam is designed as a detector for relatively lower X-ray energies, and the device impacted second is designed as a detector for relatively higher X-ray energies. In a known manner, an average atomic number (ordinal number) of the material of the item located in the primary beam is additionally determined.

The diffraction apparatus is preferably mounted adjustably in an X-ray testing machine, with the collimator/detector arrangement furthermore being adjustable in height relative to the X-ray source.

The collimator/detector arrangement further comprises a circular-slot collimator having an energy-sensitive detector behind it.

The invention is de-scribed below in detail by way of an embodiment illustrated in the drawings.

DETAILED DESCRIPTION OF THE PREFERRED EMBODIMENTS

Figure 1:
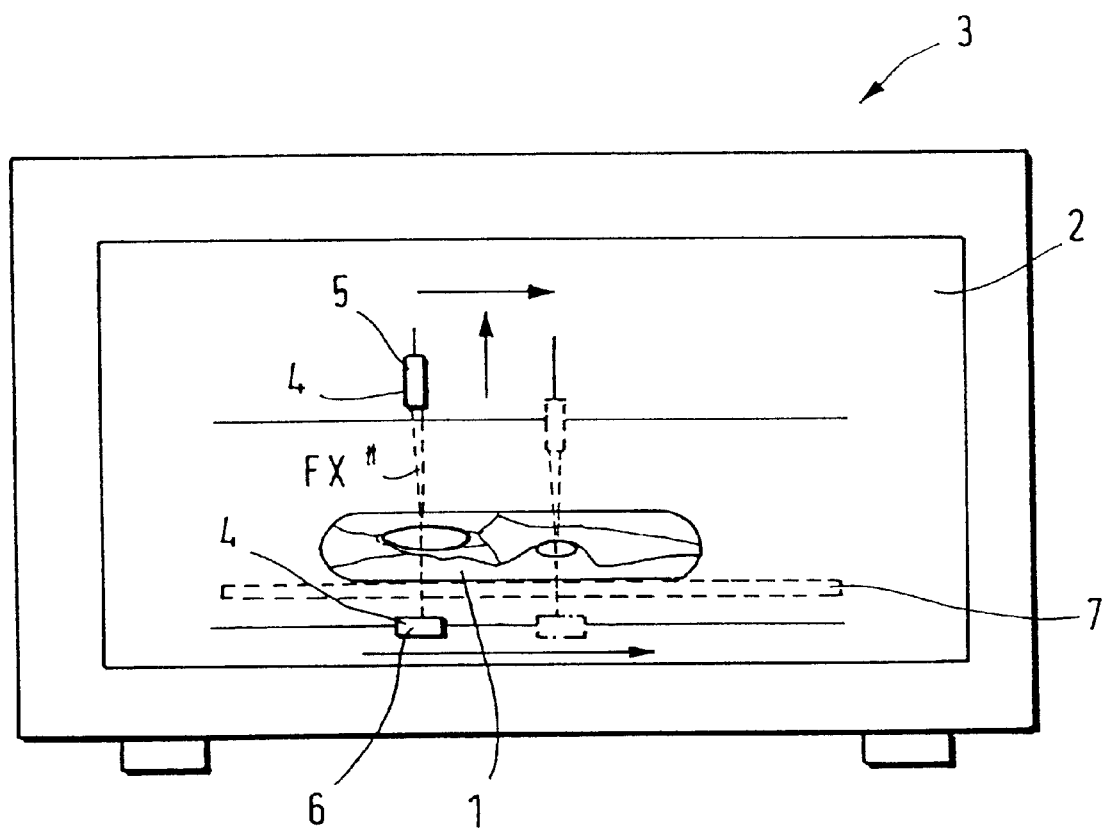
FIG. 1 is a schematic representation of an embodiment of the invention in an X-ray testing machine.

As shown in FIG. 1, an object 1 to be X-rayed is located in an X-ray tunnel 2 of an X-ray testing machine 3. Located inside the X-ray tunnel 2 is a diffraction apparatus 4, comprising a collimator/detector arrangement 5 and an X-ray source 6. The collimator/detector arrangement 5 is directed to a primary beam FX', a "pencil beam," of an X-ray bundle of this X-ray source 6, which, in this embodiment, is preferably disposed beneath a transport device 7 for an object to be transported in the X-ray tunnel 2. The collimator/detector arrangement 5 preferably can be adjusted in height relative to the X-ray source 6.

Figure 2:
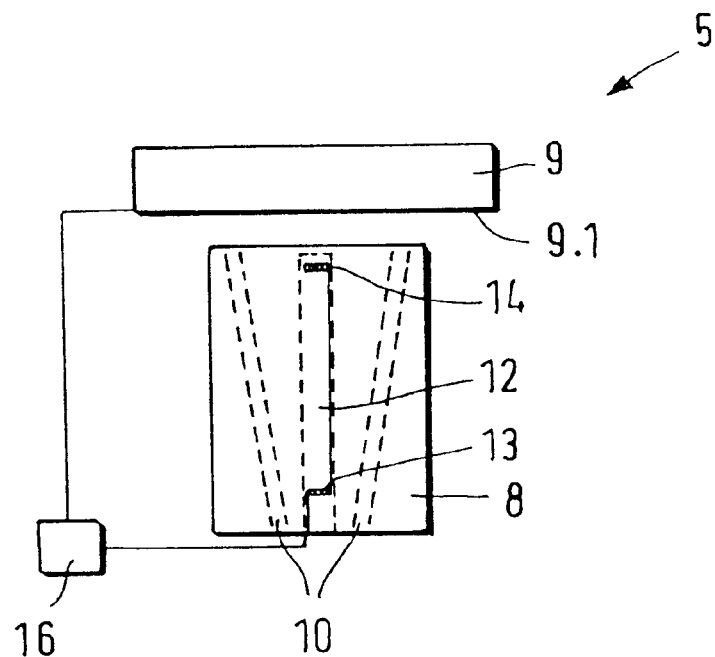
FIG. 2 further illustrates the apparatus of the invention of FIG. 1 in more detail.
Figure 2:
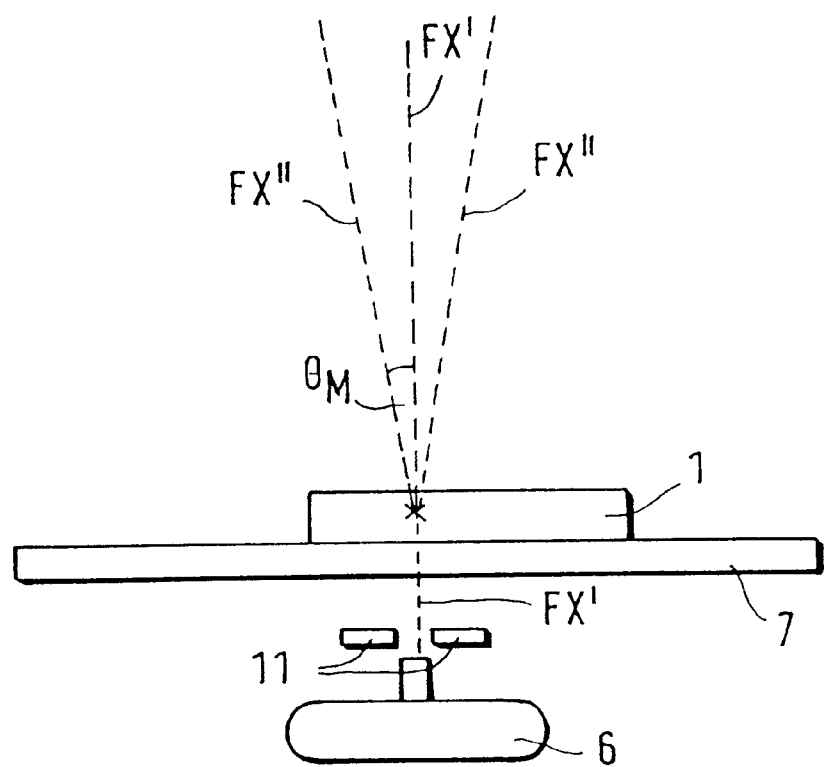

FIG. 2 shows parts of the diffraction apparatus 4 in greater detail.

The collimator 8 comprises a circular slot 10 in the form of a truncated cone such that, of the scatter radiation emanating from the tested point of the object, only the components that fall within a specific angle $\Theta_M$ are allowed through. The energy-sensitive detector 9 located behind the collimator 8 thus detects only radiation FX" which is scattered with an angle $\Theta_M$ at the object. To attain a primary beam FX' for this testing process a collimator arrangement 11, for example an aperture-plate arrangement, is mounted in front of the X-ray source 6.

If the primary beam FX' impacts a material, this primary beam FX' is known to be partially deflected at the crystal-lattice structure of the material (Bragg's Law) as scatter radiation FX". Accordingly, the energy spectrum obtained with the energy-sensitive detector 9 reveals the crystal structure of the material, and thus the identity of the material. In particular, explosives can be identified and distinguished in this manner.

According to the method, in the first step, the material is X-rayed by the primary beam FX', and in which as a second step, the primary beam FX' is diffracted at the material, thereby producing a diffraction spectrum, which is measured with the detector 9 in a third step. In a fourth step, this measured energy spectrum or diffraction spectrum is compared to known diffraction spectra that are stored in the computer 16 for determining the type of material in a fifth step.

In practice, the measured diffraction spectrum is influenced by the absorption behavior of the material in a fifth step located in the beam path of the primary beam FX'. For assessing and considering this influence, a central, bore-like opening 12 acting as a central collimator, is cut into the collimator 8, the opening being closed against the detector 9 disposed behind it, i.e., a blind bore. Disposed in the opening 12 are a first detection device 13 and, behind it at a defined distance, a second detection device 14. The first detection device 13 is designed as a detector for relatively lower X-ray energies, and the second detection device 14 is designed as a detector for relatively higher X-ray energies.

These detection devices 13, 14 can be used in a conventional manner to measure the absorption behavior of the material and, from this, to determine in a computer 16 the average atomic number of the material according to, for example, a multi-energy measurement method. In the presence of a highly-absorbent material, lower-energy diffraction lines disappear in the diffraction spectrum of the material to be determined, so the corresponding diffraction lines are missing in the measured energy spectrum or diffraction spectrum. This information can be supplied to the computer 16, which then classifies these as missing, for example, and therefore as diffraction lines that are not to be tested in the evaluation of the energy spectra. In this way, an improved identification of the material is attained with the combination of the average atomic number and the determined energy spectrum or diffraction spectrum.

The collimator/detector arrangement 5 and the X-ray source 6 are mounted to be adjusted in the X-ray testing machine 3, and are preferably guided synchronously for determining the material of an item. This is effected, for example, by way of linear guidance having a spindle drive, not shown, which are actuated centrally by the computer 16.

In principle, the detection devices can also be used in other diffraction apparatuses whose primary beam is configured differently, in which case the detectors 13 and 14 must accordingly be directed to the primary beam.

The invention now being fully described, it will be apparent to one of ordinary skill in the art that many changes and modifications can be made thereto without departing from the spirit or scope of the invention as set forth herein.

What is claimed is:

1. A method for determining a material of a detected item in an object comprising:

irradiating the material with a primary X-ray beam;

measuring a diffraction spectrum of the material, with the spectrum comprising X-rays of the primary beam diffracted at the material;

measuring an X-ray absorption of the material and an average atomic number of the material by measuring X-rays of the primary beam transmitted through the material;

determining the average atomic number of the material from the measured absorption;

comparing the measured diffraction spectrum and determined average atomic number of the material to known diffraction spectra and known average atomic numbers of known materials.

2. The method according to claim 1, wherein the average atomic number is determined by a multi-energy method.

3. The method according to claim 1, wherein the comparing step comprises comparing the measured diffraction spectrum only with the known diffraction spectra of known materials having an average atomic number approximately the same as the determined average atomic number.

4. The method according to claim 1, wherein the comparing step comprises comparing the measured diffraction spectrum with known diffraction spectra only within energy ranges not substantially absorbed by the material.

5. The method according to claim 1, wherein the object is luggage.

6. An apparatus for determining a material of a detected item in an object comprising a diffraction apparatus and a computer connected thereto, and wherein said diffraction apparatus comprises an x-ray source for producing a primary x-ray beam and a collimator/detector arrangement positioned to receive the primary x-ray beam after passing through an object and including a detector and a collimator;

said detector comprises an X-ray detector positioned downstream of the collimator and having an x-ray sensitive surface oriented toward the collimator;

said collimator has a central, blind-bore closed at the end facing the detector and at least one conically expanding circular slot that defines a predetermined angle and is oriented toward said X-ray sensitive surface of the detector; and first and second spaced detection devices mounted within the blind bore and connected to the computer, with said first and second detection devices detecting relatively lower and relatively higher energy X-rays, respectively, and being spaced in the central opening such that the second detection device located behind the first detection device.

7. The apparatus according to claim 6, wherein the collimator/detector arrangement is oriented toward the primary beam of the X-ray source, and is alignable such that the primary beam passes into the central opening.

8. The apparatus according to claim 6, wherein the X-ray source is laterally adjustable, and the collimator/detector arrangement is adjustable in height relative to the X-ray source and adjustable laterally in synchronization with lateral adjustments of the X-ray source.

* * * * *